United States Patent

Iseberg

[11] Patent Number: 5,954,669
[45] Date of Patent: Sep. 21, 1999

[54] HAND-HELD HEARING SCREENER APPARATUS

[75] Inventor: Steve Iseberg, Rolling Meadows, Ill.

[73] Assignee: Etymotic Research, Inc., Elk Grove Village, Ill.

[21] Appl. No.: 08/832,277

[22] Filed: Apr. 3, 1997

[51] Int. Cl.⁶ ..................................................... A61B 5/00
[52] U.S. Cl. ............................................. 600/559; 73/585
[58] Field of Search ................................... 128/864–868; 600/559; 73/585

[56] References Cited

U.S. PATENT DOCUMENTS

| | | | |
|---|---|---|---|
| 3,295,513 | 1/1967 | Dippolito | 600/559 |
| 3,882,848 | 5/1975 | Klar | 600/559 |
| 4,057,051 | 11/1977 | Kerouac | 600/559 |
| 4,592,370 | 6/1986 | Lee | 600/559 |
| 5,738,633 | 4/1998 | Christiansen | 600/559 |

*Primary Examiner*—Michael A. Brown
*Attorney, Agent, or Firm*—McAndrews, Held & Malloy, Ltd.

[57] ABSTRACT

A hearing screener apparatus is provided. The hearing screener includes a housing, a testing probe and an elastic coupler suspending the testing probe from the housing. The testing probe preferably includes a microphone housing having a first end and a second end. A cavity extends longitudinally into the first end of the microphone housing, and a microphone is mounted to the housing adjacent the cavity. An ear tip is fitted onto the first end of the microphone housing for insertion into a patient's ear. The ear tip preferably has a flexible flange arranged at its end to seal within the ear canal of the patient. A further elastic coupler suspends the ear tip assembly from the testing probe. Preferably, the elastic coupler is a number of elastic bands or o-rings distributed to concentrically suspend the probe within the housing. The screener allows the testing probe to be manipulated about all axes and has an isolation body which is also capable of being manipulated relative to the housing. The elastic couplers provide vibrational noise isolation due to movement of the patient and the user.

26 Claims, 6 Drawing Sheets

HAND-HELD HEARING SCREENER APPARATUS

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

The present invention relates generally to hearing test devices and more specifically to an infant hearing screener which uses distortion-product otoacoustic emissions (DPOAE) to determine the function of the outer hair cells, which is an indication of middle-ear function. For example, the absence of DPOAE indicates a possible hearing loss.

The otoacoustic emissions produced by a healthy ear are extremely small in magnitude. The emissions typically range from −10 db SPL to +20 db SPL. Any kind of extraneous noise introduced into the ear canal or measurement system can mask these emissions and give a false negative response. The microphone must have a very low internal noise level to discriminate the emissions from the system noise. All existing equipment for testing for DPOAE uses a probe which seals into the ear canal and is attached to the measurement equipment through a cable. This type of system is not practical in an infant screener for several reasons.

These reasons include the fact that an infant's ear canal is very small, and as a result, it can be quite difficult to seal a probe into such a small canal any pull on the probe from the attached cable can break the seal or pull the probe out of the canal. In addition, the time required to place a probe in the infant's ear canal significantly slows down the testing process. Typically, the infant is asleep when the testing is performed so that movement is minimal. The process of putting the probe into the infant's ear canal in a manner so that it stays for the duration of the test often wakes the infant which, of course makes the test difficult or impossible to perform.

While a hand-held screening device alleviates many of the above discussed problems, implementation of such a device has inherent problems which must be overcome to provide an effective hearing measurement device. One such problem results from the vibrational noise generated by the tester's hand during the testing. This noise is transmitted through the device and into the microphone which prevents accurate measurements. Holding a conventional probe to the ear canal creates a noise level that completely masks any emissions that could otherwise be detected.

Another problem is the difficulty in achieving a consistent seal to the infant's ear canal. Difficulty in maintaining the seal results from minor movements of the infant's head and/or the tester's hand. An embodiment of the screener solves the above problems, thereby providing a screener for performing DPOAE testing quickly and easily.

BRIEF SUMMARY OF THE INVENTION

The present invention is an infant hearing screener which uses distortion-product otoacoustic emissions (DPOAE) to determine the function of the outer hair cells within the middle ear structure. The function of the outer hair cells is an indication of middle-ear function; the absence of DPOAE indicates a possible hearing loss.

The infant screener is hand-held device that couples to the infant's ear to perform DPOAE testing. The device creates tones and administers them to the ear canal through two receivers. The emissions are then picked up through a low-noise microphone, and analyzed by a built-in digital signal processor (DSP). The result is displayed on a liquid crystal display (LCD) and can be printed by infrared link to a separate hand-held printer.

The infant screener uses a different approach for sealing to the ear canal that solves the problems in prior devices listed above. This design has a testing probe mechanically attached to the measurement system making a single hand-held device that is partially inserted directly into the infant's ear canal. Such an arrangement negates the need for an external cable interconnection.

An embodiment of the screener includes an assembly to maintain sealing contact in the ear canal. In addition, the screener includes a vibrational noise isolating microphone assembly. In an embodiment, the screener isolates noise generated by the slight tremor and movement that typically results in a normal human hand.

To this end, the tester can hold the hearing testing device to the ear canal and vibrational noise is isolated by attaching the microphone assembly to the hand-held instrument with a mesh of compliant elastomer o-rings. The o-rings are coupled to the microphone housing in a circular pattern designed to give the microphone assembly movement on all axes. The vibrational noise generated by the hand is thereby damped through the o-rings. This formation minimizes the induced vibrational noise that is transmitted into the microphone assembly.

In addition, maintaining a good seal to the ear canal is critical to the ability to measure otoacoustic emissions. This is made easier by the screener which allows movement of the ear tip on the x and y axis. The screener also helps achieve the proper pressure on the entrance of the ear canal to effect the sealing and prevent uncomfortable pressures.

An embodiment of the screener includes an assembly of o-rings which hold the microphone and ear tip assembly to the isolation mechanism described above. These o-rings flex to allow the tip to move and keep it centered within the isolation mechanism. The amount of flex in the o-rings determines the ease of movement and can be manipulated by choosing o-rings of different materials and different durometer. This selection process is important because choosing the right material will allow for a consistent and comfortable pressure on the ear canal even when there are slight movements of the tester's hand, or of the patient's head.

When measuring otoacoustic emissions it can be difficult to know what noise is in the ear canal and what the source of the noise is. The two possible sources of the noise are biological and environmental. The infant hearing screener allows the user to listen to the noise level in the ear canal before testing and between tests. Doing so gives the tester the feedback necessary to know how to hold the screener against the patient's ear and how much pressure is necessary to maintain the seal at the entrance of the ear canal. The user can also listen to the actual emissions generated by the ear.

DETAILED DESCRIPTION OF THE INVENTION

A hearing screener apparatus which uses distortion product otacoustic emissions (DPAOE) to determine the function of the outer hair cells, which is an indicator of middle ear function, is provided. The hearing screener is preferably a hand-held device that couples to an infant's ear to effectively perform DPAOE testing for possible hearing loss. An embodiment of the screener includes an assembly to maintain sealing contact in the ear canal of the patient as well as isolating vibrational noise from their microphone assembly caused by the tester.

Figure 1A:
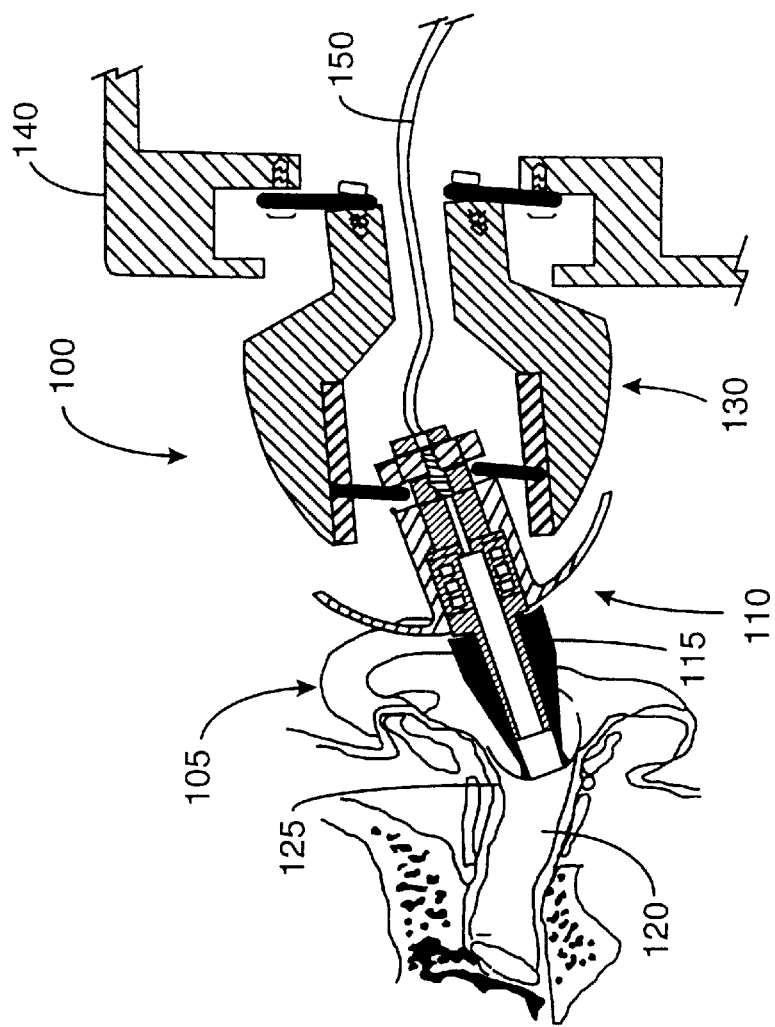
FIG. 1A is a side view in cross-section of an embodiment of the hearing screener arranged in a patient's ear canal.
Figure 1B:
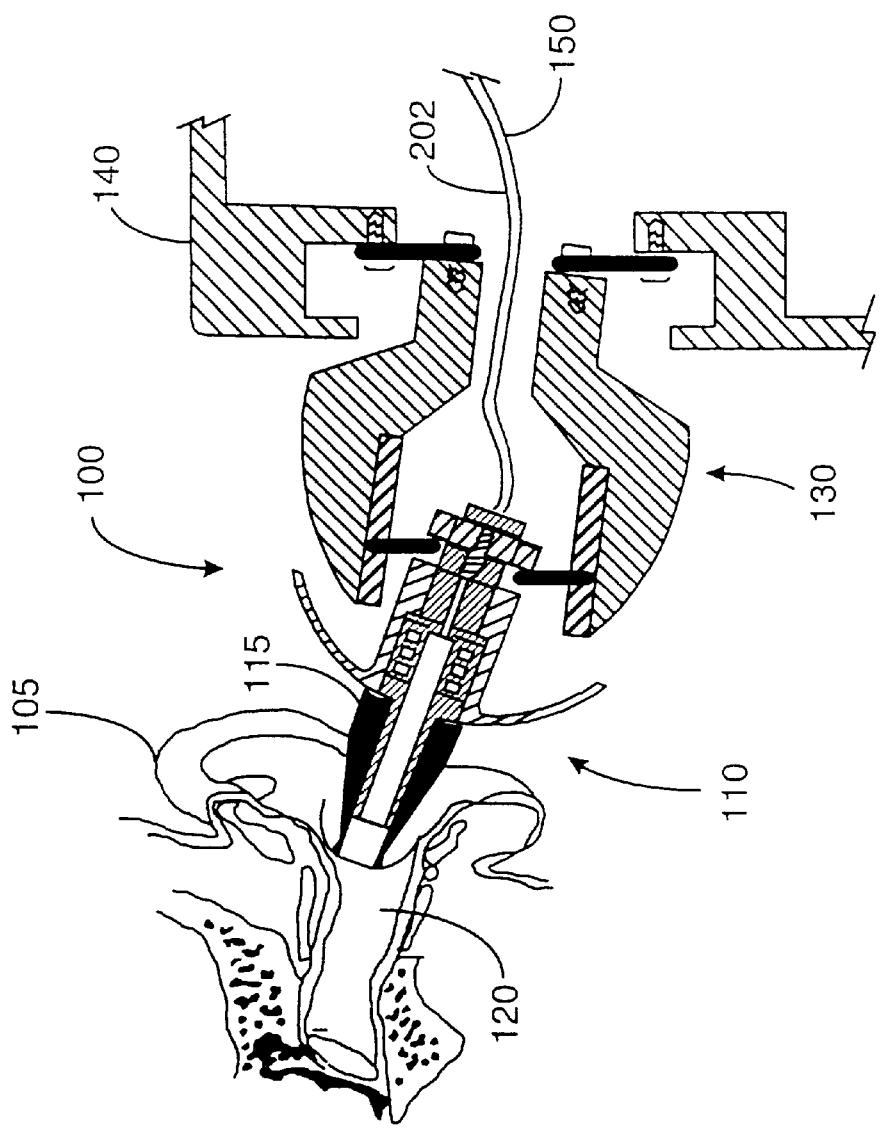
FIG. 1B is a side view in cross-section of an embodiment of the hearing screener arranged in a patient's ear canal.

Referring now to the figures, FIG. 1A is a side view in cross-section of an embodiment of the hearing screener arranged in a patient's ear canal. FIG. 1B is a similar side view of the hearing screener arranged at a different angle of attack into the patient's ear canal. An embodiment of the hearing screener is referenced generally at 100. A patient's ear 105 is also illustrated. The hearing screener 100 includes a testing probe indicated at 110. The testing probe 110 includes an ear tip 115. The ear tip 115 is arranged at the entrance of an ear canal 120 as shown in FIGS. 1A and 1B. As illustrated, the ear tip 115 includes a curved flange 125 to effectively seal the car canal 120, thus effectively coupling the testing probe 110 of the hearing screener 100 with the patient's ear 105 so that proper testing can be performed.

FIGS. 1A and 1B also include an isolation body 130 and a housing 140. Also, a connection 150 is illustrated. The components of the hearing screener 100 are described in more detail below with reference to FIGS. 2 and 3.

Figure 2:
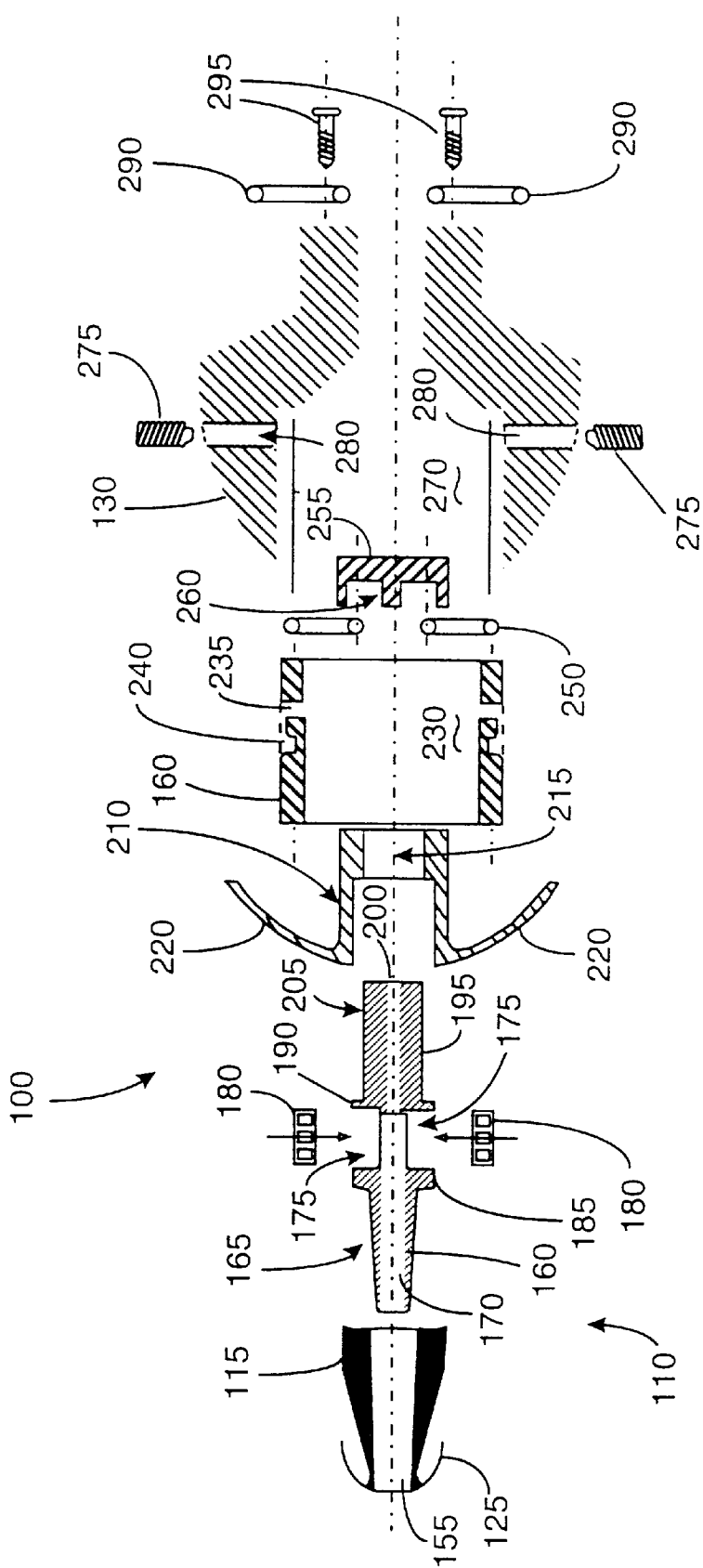
FIG. 2 is an exploded cross-sectional side view of an embodiment of the present invention.

FIG. 2 illustrates an exploded side view of an embodiment of the hearing screener 100 of the present invention. For clarity, the housing 140 is not shown in FIG. 2. As discussed above, the hearing screener 100 includes the testing probe 110, the isolation body 130 and a cylindrical coupling sleeve 160 disposed between the probe 110 and the body 130.

Proceeding from left to right in FIG. 2, the hearing screener 100 comprises the ear tip 115 having the curved flange 125 to enable proper sealing within a patient's ear canal as illustrated in FIGS. 1A and 1B and described above. The curvature of the flange 125 permits the ear tip 115 to be arranged at various angles in the patient's ear canal 120 as shown in FIGS. 1A and 1B. This is beneficial when the patient moves or when the tester needs to position the screener 100 at the proper angle for taking accurate readings. The ear tip 115 also includes a longitudinal throughbore 155. The throughbore 155 is dimensioned to accept a first end 160 of a microphone housing 165. The first end 160 of the microphone housing 165 includes a longitudinal cavity 170. The microphone housing 165 also includes a recess 175 for receiving a microphone 180 therein. FIG. 2 illustrates an embodiment in which two microphones are used. However, one or more microphones may be used in the present invention. The microphones 180 are held in the recess 175 which is defined by a first shoulder 185 and a second shoulder 190. The shoulders 185, 190 protect the microphones 180 as well as provide a defined volume in which the microphones 180 may be located. The microphone housing 165 also includes a cylindrical second end 195 having a bore 200. The bore 200 is designed to receive the connection 150 (see FIG. 1) which preferably includes one or more sound tubes 202 (see FIG. 4A) and electrical connectors 204 for transmitting electrical signals from the microphones 180. In addition, the cylindrical second end 195 of the microphone housing 165 includes a circumferential notch 205. The notch 205 is explained further below with reference to FIG. 3.

Continuing to the right of FIG. 2, the hearing screener 100 also includes a microphone housing support member 210 having a through hole 215 for receiving the second end 195 of the microphone housing 165 therethrough. The support member 210 also includes a curved flange 220. The flange 220 acts as a shield to prevent debris from entering the various components of the hearing screener 100. The shielding ability is illustrated in more detail in FIG. 3, in which the hearing screener 100 is assembled.

In addition, the cylindrical coupling sleeve 160 is shown in FIG. 2. The coupling sleeve 160 has a open interior 230. An L-shaped notch 235 having a cavity 240 is also illustrated. A plurality of o-rings 250 fit within the L-shaped notch 235 and are seated in the cavity 240. In addition, a retaining cap 255 is provided. The retaining cap 255 slips over the cylindrical second end 195 of the microphone housing 165 as illustrated more fully in FIG. 3 and captures the o-rings 250 by tabs 260 formed in the retaining cap 255.

Also shown in FIG. 2 is the isolation body 130 which has a cylindrical bore 270 for receiving the cylindrical coupling sleeve 160 therein. The coupling sleeve 160 is held securely in the isolation body 130 by set screws 275 which are tightened into threaded holes 280 formed in the isolation body 130. A second set of o-rings 290 is secured to the isolation body 130 by screws 295. The screws 295 bore into the isolation body 130. Further, the exploded assembly of FIG. 2 is illustrated in an assembled state in FIG. 3.

Figure 3:
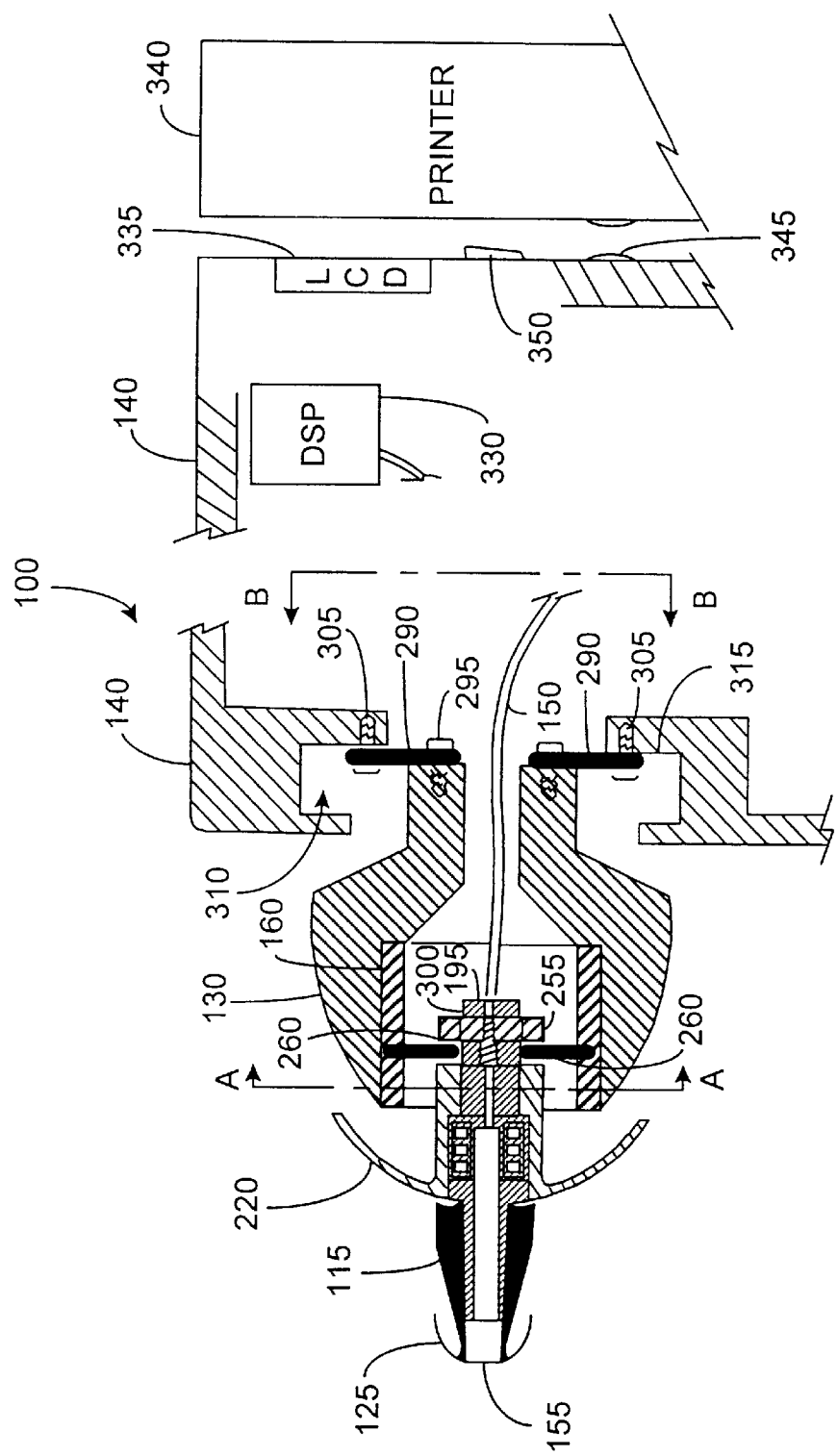
FIG. 3 illustrates a cross-sectional side view of an embodiment of a hearing screener of the present invention.

FIG. 3 illustrates an assembled embodiment of the hearing screener 100 of the present invention wherein like parts are represented by like numerals. As illustrated, when the components are assembled, the first end 160 of the microphone housing 165 fits inside the throughbore 155 of the ear tip 115. In addition, the microphone housing 165 fits in the through hole 215 of the microphone housing support member 210. In particular, the second end 195 of the microphone housing 165 passes through the support member 210 and the retaining cap 255 so that the circumferential notch 205 located adjacent the second end 195 of the microphone housing 165 is exposed past the retaining cap 255. Thus, a retaining clip 300 can be clipped around the second end 195 of the microphone housing 165 and reside within the circumferential notch 205 to secure the testing probe 110 assembly together.

As illustrated, the o-rings 250 are secured at one end by the cylindrical coupling sleeve 160 and at the other end by the retaining cap 255. In particular, one end of each o-ring 250 is held in the cavity 240 of the L-shaped notch 235 of the cylindrical coupling sleeve 160. Another end of each o-ring is held by tabs 260 of the retaining cap 255. The second set of o-rings 290 is also illustrated in a connected state in FIG. 3. The screws 295 hold one end of the o-ring 290 to the isolation body 130. In addition, screws 305 secure the other end of the o-rings 290 to the housing 140. The housing 140 also has a cavity 310 and a mounting surface 315. The screws are preferably screwed into the mounting surface 315 of the housing 140.

FIG. 3 schematically illustrates further components of the hearing screener 100. For example, a digital signal processor 330 is built into the housing 140. Also an LCD display 335 is arranged in the housing to provide measurement data as a display to the user. Further, a printer 340 may be used to print out data obtained during the hearing testing. The printer 340 is preferably a small infrared type printer. Also, an infrared connection 345 between the hearing screener 100 and the printer 400 is provided. Also operator control 350 are provided on the housing 140.

FIG. 3 illustrates the hearing screener 100 in a position in which the longitudinal axes of the components is perpendicular to the housing 140. The two sets of o-rings 250, 290 provide free movement about all axes for the testing probe portion 110 of the screener 100, as well as the isolation body 130. However, as FIGS. 1A and 1B indicate, the testing probe 110 can be displaced at an angle relative to the isolation body 130, which in turn can also be displaced at an angle relative to the housing 140. Such compound angular displacements advantageously provide manipulation of the hearing screener 100 to facilitate easy use of the device. Such manipulation capability is provided by the arrangement of the o-rings 250, 290. Embodiments of the arrangement for the o-rings are illustrated in FIGS. 4A and 4B.

Figure 4A:
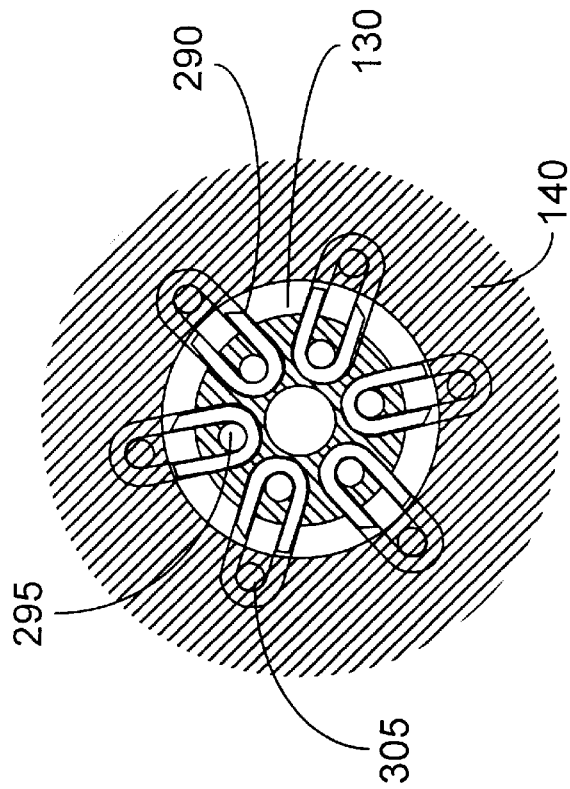
FIG. 4A is a cross-sectional view of a portion of the hearing screener taken along line A—A of FIG. 2.

For example, FIG. 4A illustrates a cross-section view of the arrangement of o-rings 250 which connect the microphone housing 165 to the coupling sleeve 160 within the isolation body 130. FIG. 4A is taken along section line A—A in FIG. 3. As shown, four o-rings 250 are equally distributed between coupling sleeve 160 and the second end 195 of the microphone housing 165. In this manner, the microphone housing 165 is concentrically suspended within the coupling sleeve 160. As discussed above, one end of the o-ring 250 is held within the coupling sleeve 160 by being captured within the L,-shaped notch 235 and residing in the recess 240. The other end of the o-ring 250 is captured by the tab 260, which is part of the retaining cap 255. Also, the coupling sleeve 160 is maintained within isolation body 130 by the set screws 275. The set screws 275 are tightened down within the screw holes 280 to secure the sleeve 160 within the isolation body 130.

Figure 4B:
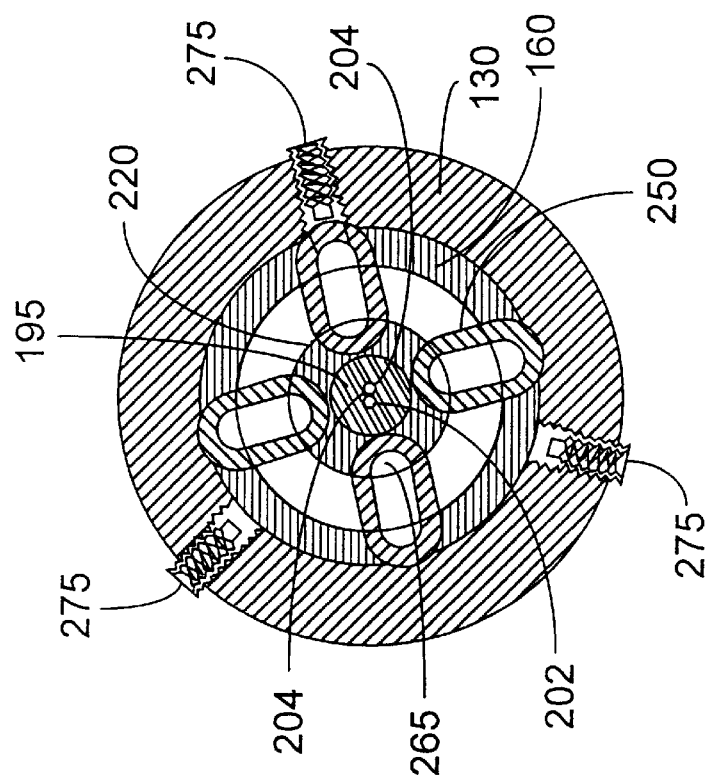
FIG. 4B is a cross-sectional view of a portion of the hearing screener taken along line B—B of FIG. 2.

FIG. 4B also illustrates the plurality of o-rings 290 distributed between the isolation assembly 130 and the housing 140. FIG. 4B is taken along section line B—B of FIG. 3. As illustrated, six o-rings 290 are mounted by screws 295 which attach to the isolation body 130 and screws 305 which attach to the mounting surface 315 of the housing 140. The isolation body 130 is thus concentrically suspended within the housing 140 by the six o-rings 290. As illustrated in FIGS. 4A and 4B, the number of o-rings may be chosen for a particular application. Also, the elasticity of the o-rings may be selected for a particular use and resiliency desired. In a preferred embodiment, o-rings of 70 durometer SHORE A provide a sufficient resiliency and feel. However, the number and elasticity of the o-rings may be chosen depending on the application desired.

Figure 5:
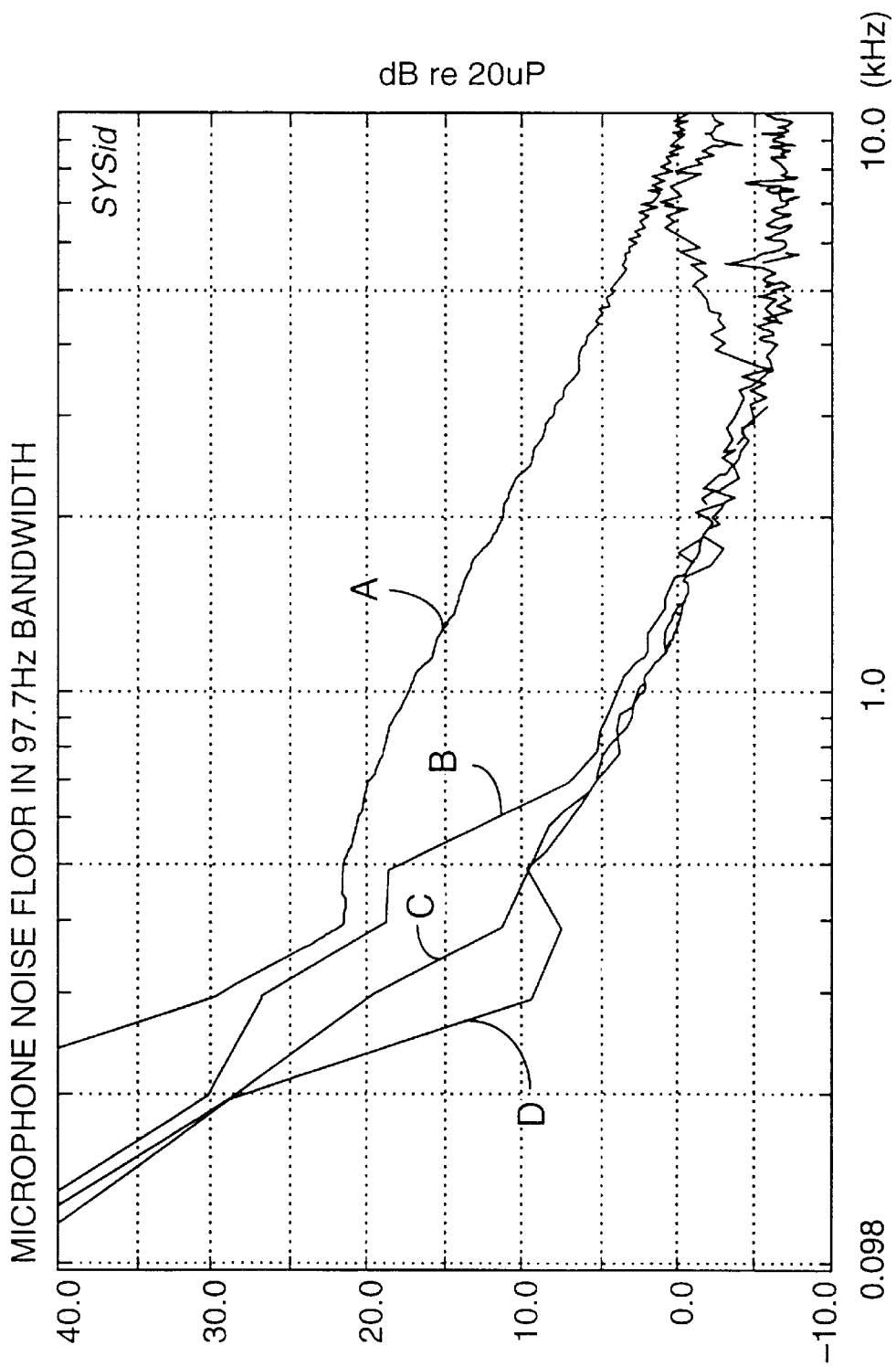
FIG. 5 is a graph illustrating various microphone noise floor levels of the present invention.

As set forth above, vibrations caused by the user holding onto the screener apparatus 100 are translated into noise. An advantage of the present invention is a dampening of this noise so that it does not interfere with the measurements being taken. FIG. 5 graphically illustrates how this elimination of the vibrational noise is accomplished.

FIG. 5 is a graph illustrating microphone noise various curves plotted for different measurement situations. The Y axis is dB and the X axis is frequency in kilohertz (kHz). The various curves illustrate experimental data taken as different parts of the hearing screener 100 are held by a tester. For example, curve A illustrates the microphone noise floor with the tester holding the ear tip 115 assembly of the hearing screener 100. Thus, the first set of o-rings 250 and the second set of o-rings 290 are rendered inoperable. Similarly, curve B illustrates the microphone noise floor when the tester holds the isolation assembly 130 of the hearing tester 100. In this situation, the first set of o-rings 250 is operable, but the second set of o-rings 290 is not. Finally, curve C illustrates a microphone noise floor curve when the tester holds the hearing screener 100 by the housing 140 as intended during a typical use. Thus, both sets of o-rings 250, 290 are operable.

As a basic reference, curve D illustrates the microphone noise for a microphone, such as an ER-10C microphone. The ER-10C microphone has the same effective noise floor as an industry standard microphone. Thus, FIG. 5 illustrates that the isolation effects of the o-rings 250 and 290, along with the arrangement of the preferred embodiment discussed above, yields a microphone noise floor virtually identical to that of the industry standard microphone when the hearing screener 100 is held by the housing 140 as illustrated in curve C. Curve A illustrates that holding the ear tip assembly 115 of the hearing screener 100 prevents the benefits of the o-rings 250, 290 from being exploited. As a result, the noise floor is approximately 15 dB more than that experienced in curve C.

Thus, as described above and graphically illustrated in FIG. 5, the first set of o-rings 250 isolate movements of the patient which cause noise, and the second set of o-rings 290 isolate hand vibration which causes noise. Together, the reduction in noise is sufficient for allowing the hand-held hearing screener 100 of the preferred embodiment discussed above to be used for taking accurate measurements of otacoustic emissions.

While particular elements, embodiments and applications of the present invention have been shown and described, it will be understood, of course, that the invention is not limited thereto since modifications may be made by those skilled in the art, particularly in light of the foregoing teachings. It is therefore contemplated by the appended claims to cover such modifications as incorporate those features which come within the spirit and scope of the invention.

I claim:

1. A hearing screener apparatus comprising:
    a housing;
    a testing probe; and
    an elastic coupler suspending the testing probe from the housing, the elastic coupler enabling the testing probe to be moved relative to the housing during use without the testing probe directly contacting the housing.

2. The apparatus of claim 1, wherein the elastic coupler comprises a plurality of elastic bands.

3. The apparatus of claim 1, wherein the testing probe further comprises:
    a microphone housing having a first end and a second end;
    a cavity extending longitudinally into the first end of the microphone housing;
    a microphone mounted to the microphone housing, the microphone arranged adjacent a portion of the cavity; and
    an ear tip fitted onto the first end of the microphone housing.

4. The apparatus of claim 3, further comprising a flange arranged at an end of the ear tip.

5. The apparatus of claim 3, further comprising a curved flange arranged at an end of the ear tip.

6. The apparatus of claim 3, further comprising a flexible flange arranged at an end of the ear tip.

7. The apparatus of claim 3, further comprising a flange arranged at an end of the ear tip, the flange angling back toward the ear tip.

8. The apparatus of claim 1, further comprising:

an ear tip assembly; and a further elastic coupler suspending the ear tip assembly from the testing probe.

9. The apparatus of claim 8, wherein the further elastic coupler comprises a plurality of elastic bands.

10. The apparatus of claim 1, further comprising:

a retaining cap constructed and arranged to capture an end of the elastic coupler; and a cylindrical coupling sleeve having a notch sufficient to capture another end of the elastic coupler.

11. The apparatus of claim 1, wherein the testing probe further comprises:

a microphone housing having a first end and a second end;

a microphone housing support member having a through hole, the second end of the microphone housing passing through the through hole; and a retaining cap fitted over the second end of the microphone housing such that an end of the elastic coupler suspending the testing probe from the housing is captured between the retaining cap and the microphone housing support member.

12. The apparatus of claim 11 further comprising:

a tab formed in the retaining cap.

13. The apparatus of claim 11 further comprising:

an isolation body elastically coupled to the housing, the isolation body including a cylindrical bore;

a coupling sleeve arranged within the cylindrical bore of the isolation body, the coupling sleeve having a notch sufficient for receiving the elastic coupler therein.

14. The apparatus of claim 13 wherein the elastic coupler concentrically suspends the microphone housing within the coupling sleeve.

15. The apparatus of claim 13 wherein the elastic coupler is a plurality of resilient o-rings.

16. The apparatus of claim 13 further comprising a further plurality of o-rings elastically coupling the isolation body to the housing.

17. The apparatus of claim 1 further comprising a plurality of o-rings distributed between the housing and the testing probe.

18. The apparatus of claim 17 wherein the plurality of o-rings allows movement of the testing probe on all axes.

19. A hearing screener apparatus comprising:

a housing;

at least one isolation body elastically coupled to the housing; and a testing probe elastically coupled to the isolation body, the isolation body preventing direct contact between the testing probe and the housing and assisting to provide movement of the testing probe relative to the housing during use by manipulation of the housing.

20. A hearing screener apparatus comprising:

a housing;

a microphone isolation assembly flexibly attached to the housing; and an ear tip assembly flexibly attached to the microphone isolation assembly, the microphone isolation assembly preventing direct contact between the ear tip assembly and the housing and assisting to reduce transmission of vibration from the housing to the ear tip assembly.

21. A hearing screener apparatus comprising:

a housing;

at least one isolation body;

a first plurality of couplers suspending the isolation body from the housing and enabling movement of the isolation body relative to the housing;

a testing probe; and a second plurality of couplers suspending the testing probe from the isolation body and enabling movement of the testing probe relative to the isolation body.

22. The hearing screener apparatus of claim 21 further comprising at least one microphone.

23. The hearing screener apparatus of claim 22 wherein the first plurality of couplers reduce transmission of vibration from the housing to the microphone.

24. The hearing screener apparatus of claim 22 wherein the second plurality of couplers reduce transmission of vibration from the testing probe to the microphone.

25. A hearing screener apparatus comprising:

a housing;

at least one isolation body elastically coupled to the housing;

a testing probe elastically coupled to the isolation body; and at least one microphone, the microphone having a noise floor substantially similar to an industry standard microphone when the housing is grasped by a user.

26. A hearing screener apparatus comprising:

a housing;

at least one isolation body elastically coupled to the housing;

a testing probe elastically coupled to the isolation body; and at least one microphone, the microphone having a noise floor of at least approximately 15 dB lower when the housing is grasped by a user than when the testing probe is grasped by a user.

* * * * *